United States Patent [19]

Hakamatsuka et al.

[11] Patent Number: 4,713,006
[45] Date of Patent: Dec. 15, 1987

[54] ARTIFICIAL TOOTH ROOT

[75] Inventors: Yasuharu Hakamatsuka, Tokyo; Nobuyuki Yokoyama, Chiba, both of Japan

[73] Assignee: Olympus Optical Co., Ltd., Tokyo, Japan

[21] Appl. No.: 844,210

[22] Filed: Mar. 26, 1986

[30] Foreign Application Priority Data

Apr. 4, 1985 [JP] Japan ................ 60-71375

[51] Int. Cl.$^4$ ............ A61C 8/00; A61F 1/24
[52] U.S. Cl. ............... 433/201.1; 433/173; 433/174; 433/175
[58] Field of Search ............ 433/201, 173, 174, 175

[56] References Cited

U.S. PATENT DOCUMENTS

| 3,801,344 | 4/1974 | Dietz | 433/228.1 X |
|---|---|---|---|
| 3,973,972 | 8/1976 | Muller | 433/228.1 X |
| 4,259,072 | 3/1981 | Hirabayashi et al. | 433/201.1 X |
| 4,304,553 | 12/1981 | Heimke et al. | 433/201.1 X |
| 4,308,064 | 12/1981 | Takami et al. | 433/228.1 X |
| 4,321,042 | 3/1982 | Scheicher | 433/201.1 |
| 4,411,624 | 10/1983 | Ogino et al. | 433/201.1 X |
| 4,446,579 | 5/1984 | Inamori et al. | 433/201.1 X |
| 4,447,210 | 5/1984 | Hidaka et al. | 433/173 |
| 4,497,629 | 2/1985 | Ogino et al. | 433/201 |

FOREIGN PATENT DOCUMENTS 58-116353 7/1983 Japan .
58-118746 7/1983 Japan .

Primary Examiner—Nancy Swisher
Attorney, Agent, or Firm—Frishauf, Holtz, Goodman & Woodward

[57] ABSTRACT

An artificial tooth root is divided into a tooth root body and a root holder. The material for the artificial tooth root body is selected in consideration of its strength. The outer surface of the root holder that is in contact with the alveolar bone is formed of a biologically activated material for providing strong adhesion between the root holder and the alveolar bone. An impact reducing material is provided between the artificial tooth root body and the root holder to reduce the impact force placed on the tooth root body so that the force applied to the alveolar bone portion is reduced.

10 Claims, 8 Drawing Figures

ARTIFICIAL TOOTH ROOT

BACKGROUND OF THE INVENTION

This invention relates generally to an artificial tooth root and particularly to an artificial tooth root that has improved impact resistance.

Recently, there has been much research into dealing with natural teeth damaged through disease or accident by extracting the tooth and implanting an artificial root which has the same function as the original natural tooth.

FIGS. 1 and 2 show a prior art commercialized sapphire artificial tooth root implantation. In FIG. 1, after the damaged tooth (not shown) has been extracted as shown by the arrow, recess 4 is formed in alveolar bone portion 2 and sapphire tooth root 6 is implanted. In FIGS. 1 and 2 reference numeral 8 denotes the alveolar bone and 10 denotes the alveolar ridge or gingiva.

A metal material that is compatible with live tissue is used for artificial tooth root 6. This kind of tooth root has excellent mechanical strength but its biological bondability with live tissue is not satisfactory and, consequently, special means for fastening the tooth root are required. Metal is also not desirable in that, depending on the type of metal used, metal ions harmful to live tissue may diffuse out of the tooth root.

In recent years ceramics such as single crystal alumina have been developed for artificial tooth roots and put into practical use. These ceramic tooth roots have an advantage over metal in that there is no diffusion to harmful material into the tissue but they also provide poor bondability. Material that does provide excellent biological bonding with live tissue is ceramics such as biologically activated glass, TCP (tricalcium phosphate) or apatite. These materials, however, while having excellent biological bondability, have insufficient mechanical strength.

In the prior art it has been impossible to obtain an artificial tooth root that has both good biological bonding and good mechanical strength. There have, accordingly, been problems with impact resistance when brittle food is chewed. With a tooth root that has only mechanical strength, for example, the pressure generated from chewing is transmitted to alveolar bone 8 and the surrounding area which may be damaged by this pressure, and when used for a long period of time, may result in tooth root 6 coming loose from alveolar bone portion 2. Where the biological bonding characteristics are excellent, on the other hand, damage to the tooth root itself becomes a problem.

SUMMARY OF THE INVENTION

The object of the invention is to provide an artificial tooth root using a material that has sufficient mechanical strength such that there is no possibility of damage to the root itself or the surrounding area when a brittle substance is chewed, for example, and which will not loosen even when used for a prolonged period.

The artificial tooth root body of this invention, which is implanted in a recess formed in the alveolar bone portion, comprises: an artificial tooth root body; a root holder for insertion into a recess in the alveolar bone portion, at least that portion of the outer surface of this root holder that is in contact with the alveolar bone portion being formed of biologically activated material, and the root holder having a receiving recess into which the artificial tooth root body is fitted; and an impact reducing material, which is inserted between the artificial tooth root body and the receiving recess, which elastically bonds the tooth root body to the root holder, and which can ameliorate impacts.

According to this invention, it is possible to obtain a natural and sufficiently large artificial tooth root, regardless of the material used for the artificial tooth root body, without the nature of this material being directly relevant and without using special means to obtain a bond between the tooth root and the alveolar bone portion. When an impact force is placed on the tooth root body from chewing, the impact is absorbed by the impact reducing material. The result is that a material of sufficient mechanical strength can be used so that there is no danger of the root or of the alveolar bone and its surrounding tissue being damaged even if brittle food is chewed, and there is no danger of the artificial tooth root coming loose after prolonged use.

DETAILED DESCRIPTION OF THE PREFERRED EMBODIMENTS

Figure 1:
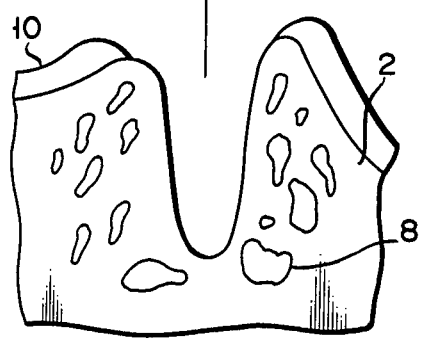
FIG. 1 shows the alveolar bone portion after a natural tooth has been extracted.
Figure 2:
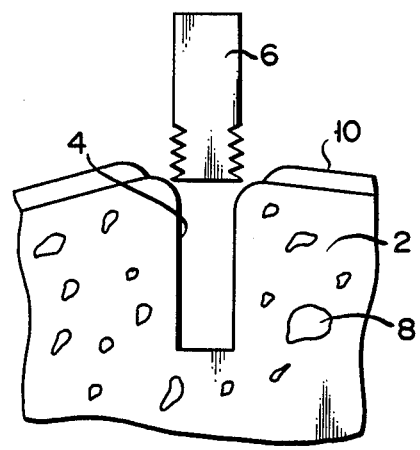
FIG. 2 shows a prior art artificial tooth root implant.
Figure 3:
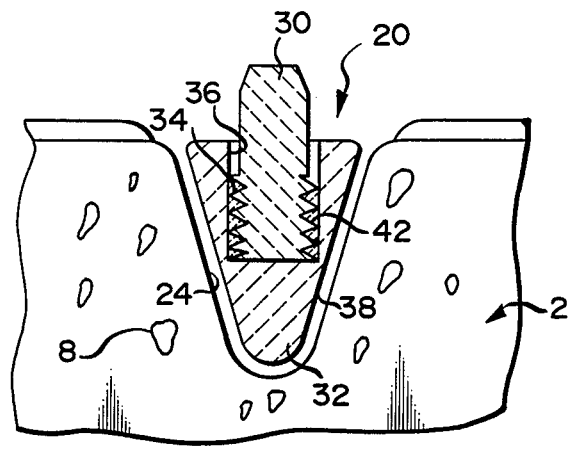
FIG. 3 shows the artificial tooth root of this invention.
Figure 4:
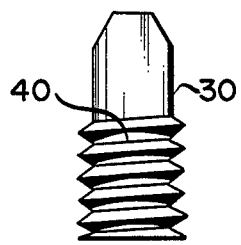
FIG. 4 is a side view of the tooth root body shown in FIG. 3.

FIG. 3 shows artificial tooth root 20 according to an embodiment of the invention implanted in alveolar bone portion 2 and FIG. 4 is an external side view of tooth root body 30 of artificial tooth root 20.

Recess 24 is left in alveolar bone portion 2 in the location where a natural tooth has been extracted. Artificial tooth root 20 includes root holder 32 which is inserted into recess 24 and tooth root body 30 which is inserted into a receiving recess 36 formed in root holder 32. Impact reducing member 34 is fitted between tooth root body 30 and the walls of the root holder deining the receiving recess 36.

Root holder 32 is formed of high strength ceramics $Al_2O_3$—$ZrO_2(Y_2O_3)$ and is covered by a biologically activated layer 38, which is made of $\beta$-TCP (tricalcium phosphate $\beta$-$Ca_3(PO_4)_2$) hydroxyapacite ($Ca_{10}(PO_4)_6(OH)_2$) or a compound thereof. Root holder 32 is implanted in recess 24 formed in alveolar bone portion 2.

Biologically activated layer 38 is formed as follows. When apatite or $\beta$-TCP is formed on the surface, water soluble calcium chloride (calcium nitrate, etc.), calcium complexing agent (ethylene jamin four vinegar chloride, ammonium chloride) and water soluble phosphate chloride (hydrogen phosphate 2 ammonium) is mixed at a mole fraction? of 1:1 to 1.2:06. A hydrogen peroxide solution is added to the water solution, which is adjusted to have a prescribed hydrogen ion density (hereinafter referred to as pH) in the 6–11 range, to a weight percent of 1–2, and the calcium phosphate solution is adjusted. The temperature is raised to 80° C., $ZrO_2$—$AkO_3(Y_2O_3)$ base material is immersed in this solution, and the calcium phosphate (hdroxyapacite or calcium phosphate) is extracted.

The base material from which calcium phosphate has been extracted is heat treated at 800° to 1200° C. to strongly adhere the calcium phosphate film to the base material.

This material layer 38 is provided between tooth root body 30 and alveolar bone portion 2 and has excellent biological bonding characteristics.

Receiving recess 36, which effectively constitutes the opening in the surface of alveolar bone portion 2 and into which tooth root body 30 is inserted, is formed in root holder 32.

Tooth root body 30 is formed of a compound material in which calcium phosphate ceramic is used, an apatite ceramic, an organic high polymer material (polymethyl methacrylate, PMMA resin), metal (Ti or Co—Cr—Mo), or inorganic material ($Al_2O_3$, $ZrO_2$, $Si_3N_4$, SiC, free cutting crystalized glass), etc. and the base of body 30 is inserted into root holder 32. The base of tooth root body 30 has a thread 40 formed in it.

Impact reducing i.e., impact absorbing material 34 is a rubber such as silicon rubber or an inorganic fiber such as ceramic fiber etc. This impact reducing or absorbing material 34 is inserted between root holder 32 and root body 30.

Root holder 32, root body 30 and impact reducing material 34 are bonded into a single unit by a high polymer type adhesive or by an inorganic adhesive.

The adhesive layer 42 has a Young's modulus of less than 0.14 kg/mm$^2$, which results in a firm bond without any slippage between root body 30, impact reducing material 34 and root holder 32. An example of this kind of adhesive is a mixture of MMA-PMMA to which tri-n-butylboron (TBB) has been added.

The artificial tooth root according to this embodiment of the invention as described above was implanted into the alveolar bone of a dog and the overall tissue structure as well the adhesion with tooth root 20 were examined with a scanning microscope after, 3, 6 and 9 weeks, and the following results were determined. It should be noted that during this period the dog's general condition was excellent.

After:
- 3 weeks—collagen tissue formed into net-like structure between root holder 32 and alveolar bone portion 2 and bone particles could be seen adhering to these structures
- 6 weeks—collagen tissue has increased density and bone particles have begun (further) settling
- 9 weeks—the mesh of the collagin tissue is now nearly filled with bone particles and formation of a bone wall has begun With the artificial tooth root of this embodiment, it is possible to obtain a natural and sufficiently large artificial tooth root, regardless of the material used for the artificial tooth root, without the nature of this material being directly relevant and without using special means to obtain a bond between the tooth root and the alveolar bone portion. It is possible to use material of sufficient mechanical strength for the tooth root so that there is no danger of the root being damaged. When an impact force is placed on the tooth root body 30 from chewing, the impact is absorbed by the impact absorbing material 34. The result is that a material of sufficient mechanical strength can be used so that there is no danger of the root or of the alveolar bone and its surrounding tissue being damaged even if brittle food is chewed, and there is no danger of the artificial tooth root 20 coming loose from alveolar bone body 2 after prolonged use.

In this invention greater impact reduction and force distribution is obtained by filling impact reducing material 34 between root body 30 and root holder 32 than by filling the material between the crown (not shown) and tooth root 20. The reason for this is that root body 30 is fastened after root holder 32 has been fastened so the area near root holder 32 absorbs less impact than the joint between root holder 32 and recess 24.

Figure 5A:
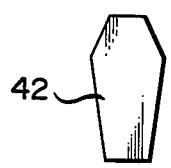
FIGS. 5A to 5D are side views of variations of the artificial tooth root.
Figure 5B:
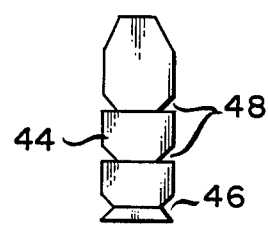
Figure 5C:
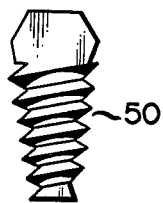
Figure 5D:
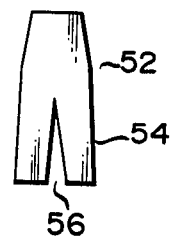

This invention is not limited to the above embodiment. For example, in the embodiment of FIGS. 3 and 4, the cross section along the axis of tooth root body 30 is substantially rectangular. However, it may have a shape as shown in FIGS. 5A to 5D. The insertion portion of tooth root body 42 in FIG. 5A is tapered. In FIG. 5B tooth root body 44 has ridge 46 at the base to prevent the root from being pulled out and a middle section that has a series of steps 48. The insertion portion of tooth root 50 in FIG. 5C is formed as a tapping screw and FIG. 5D shows an example where metal is used to form artificial tooth root 52. The base of the insertion portion in this case broadens slightly and notch 56 is formed in the center of the base to give the insertion portion opening and closing elasticity.

The shapes shown in FIGS. 5B to 5D provide increased mechanical fastening strength. In the above embodiments as well, impact absorbing material 34 is provided over the entire insertion portion. The pressure exerted on tooth root body 30 from chewing is in a direction parallel to the axis of the root so it is possible to provide impact absorbing material 34 only on and around the base of the root. It is also possible for the surface of root holder 32 to be coated with a porous material. This porous material provides easy acceptance of collagen fibers so bondability between the tissue and root holder 32 is improved. An example of porous material that may be used is $\beta$-TCP, hydroxyapacite, or a compound thereof.

This invention is not limited to the above embodiments and various modifications are possible without departing from the scope of the invention.

What is claimed is:

1. An artificial tooth root implantable in a recess formed in an alveolar bone portion, comprising:
   an artificial tooth root body;
   a root holder, which is insertable into said alveolar bone recess, at least that portion of an outer surface of said root holder that is in contact with the alveolar bone portion being formed of biologically activated material, said root holder having walls defining a receiving recess in said root holder and into which said artificial tooth root body is fitted; and
   an impact reducing means including a silicon rubber impact absorbing material and an adhesive provided between said artificial tooth root body and said walls of said root holder defining said receiving recess, for elastically boding said tooth root body to said root holder and for reducing impact on said root holder.

2. An artificial tooth root according to claim 1, wherein said root holder is made of a material selected from the group of $Al_2O_3$—$ZrO_2$ and $Al_2O_3$—$Y_2O_3$.

3. An artificial tooth root according to claim 1, wherein said biologically activated material is a material selected from the group of $\beta$-TCP, hydroxyapatite and a compound thereof.

4. An artificial tooth root according to claim 1, wherein said artificial tooth root body is formed of at least one material of a group comprising a compound material which uses a ceramic of the calcium phosphate group, an apatite ceramic, a polymethyl metacrylate, titanium, Co—Cr—Mo alloy, $Al_2O_3$, $ZrO_2$, $Si_3N_4$, SiC or a free cutting crystallized glass.

5. An artificial tooth root according to claim 1, wherein said impact absorbing material is a ceramic fiber.

6. An artificial tooth root according to claim 1, wherein said adhesive comprises an adhesive layer which adheres said impact absorbing material to the root holder and to the artificial tooth root body.

7. An artificial tooth root according to claim 6, wherein Young's modulus of said adhesive layer is less than 0.14 kg/mm$^2$.

8. An artificial tooth root according to claim 7, wherein said adhesive layer is a MMA-PMMA compound to which tri-n-butyl boron has been added.

9. An artificial tooth root according to claim 1, wherein said root holder is made of a porous material.

10. An artificial tooth root according to claim 9, wherein said porous material is a material selected from the group of β-TCP, hydroxyapacite and a compound thereof.

* * * * *